(12) United States Patent
Kraft et al.

(10) Patent No.: US 10,054,522 B1
(45) Date of Patent: Aug. 21, 2018

(54) SYSTEMS, DEVICES, AND METHODS FOR SPECIMEN PREPARATION

(71) Applicants: Colleen Kraft, Decatur, GA (US); W. Robert Taylor, Stone Mountain, GA (US); Michael L. Wach, Alpharetta, GA (US); Jonathan Shaw, Atlanta, GA (US); Louis F. Malice, Marietta, GA (US)

(72) Inventors: Colleen Kraft, Decatur, GA (US); W. Robert Taylor, Stone Mountain, GA (US); Michael L. Wach, Alpharetta, GA (US); Jonathan Shaw, Atlanta, GA (US); Louis F. Malice, Marietta, GA (US)

( * ) Notice: Subject to any disclaimer, the term of this patent is extended or adjusted under 35 U.S.C. 154(b) by 345 days.

(21) Appl. No.: 14/999,504

(22) Filed: May 16, 2016

Related U.S. Application Data (60) Provisional application No. 62/162,144, filed on May 15, 2015.

(51) Int. Cl.
| | | |
|---|---|---|
| *G01N 1/14* | (2006.01) | |
| *B01D 33/80* | (2006.01) | |
| *G01N 1/34* | (2006.01) | |
| *B01D 33/01* | (2006.01) | |
| *A61B 10/00* | (2006.01) | |

(52) U.S. Cl.
CPC ........... *G01N 1/34* (2013.01); *A61B 10/0038* (2013.01); *B01D 33/0183* (2013.01); *B01D 33/80* (2013.01); *G01N 1/14* (2013.01)

(58) Field of Classification Search
CPC ............ G01N 1/34; G01N 1/14; G01N 33/48; G01N 1/28; B01D 33/0183; B01D 33/80; B01D 35/02; A61B 10/0038; B01L 2300/0832; B01L 2400/0478; B01L 2400/0481; B01L 2400/0633; B01L 3/00; B01L 3/14
USPC ...................... 435/34; 436/174, 177; 604/403
See application file for complete search history.

(56) References Cited

U.S. PATENT DOCUMENTS

| | | | | |
|---|---|---|---|---|
| 4,007,012 A | * | 2/1977 | Greenwald | A61B 10/0038 206/229 |
| 4,010,648 A | * | 3/1977 | Harris, Sr. | G01N 1/14 141/369 |
| 4,032,437 A | * | 6/1977 | Greenwald | A61B 10/0038 209/17 |

(Continued)

OTHER PUBLICATIONS

Rohlke et al. (Ther Adv Gastroenterol, (2012) 5(6) 403-420. (Year: 2012).*

*Primary Examiner* — Matthew F DeSanto (57) ABSTRACT

Systems, devices and methods are configured to prepare a specimen. A system may include a preparation device configured to mate with a specimen collection device. The preparation device may include an agitator member and a filter member. The filter member and the agitator member may be configured to move independently with respect to each other and the preparation platform member. The filter member may be configured to move linearly with respect to the preparation platform member and/or the agitator member, and the agitator member may be configured to move linearly and radially with respect to the preparation platform member and/or the agitator member. The system may also include a specimen collection device. The specimen may include but is not limited to fecal matter.

6 Claims, 5 Drawing Sheets

(56) References Cited

U.S. PATENT DOCUMENTS

| | | | | |
|---|---|---|---|---|
| 4,067,443 | A * | 1/1978 | Greenwald | A61B 10/0038 206/229 |
| 4,293,405 | A * | 10/1981 | Greenwald | A61B 10/0038 209/17 |
| 4,678,559 | A * | 7/1987 | Szabados | G01N 1/28 209/17 |
| 4,960,130 | A * | 10/1990 | Guirguis | A61B 5/150213 422/913 |
| 4,961,432 | A * | 10/1990 | Guirguis | A61B 5/150213 422/913 |
| 4,962,044 | A * | 10/1990 | Knesel, Jr. | B01D 33/01 210/359 |
| 5,108,927 | A * | 4/1992 | Dorn | C12N 1/04 435/243 |
| 5,358,690 | A * | 10/1994 | Guirguis | A61B 10/0045 422/420 |
| 5,429,803 | A * | 7/1995 | Guirguis | A61B 10/007 422/419 |
| 5,514,341 | A * | 5/1996 | Urata | A61B 10/0038 422/534 |
| 5,578,459 | A * | 11/1996 | Gordon | B01J 3/006 135/29 |
| 6,277,646 | B1 * | 8/2001 | Guirguis | A61B 10/007 422/417 |
| 6,830,935 | B1 * | 12/2004 | El-Amin | B01F 9/06 210/767 |
| RE39,457 | E * | 1/2007 | Guirguis | A61B 10/007 422/419 |
| 7,316,779 | B2 * | 1/2008 | Pressman | B01D 61/18 210/321.75 |
| 8,845,605 | B2 * | 9/2014 | Hensler | A61M 1/0056 604/317 |
| 9,220,485 | B2 * | 12/2015 | Parks | A61B 10/0045 |
| 9,816,087 | B2 * | 11/2017 | Gellibolian | C12N 15/1017 |
| 2002/0096469 | A1 * | 7/2002 | Faulkner | A61B 10/0096 210/464 |
| 2003/0205097 | A1 * | 11/2003 | Wickstead | B01L 3/502 73/863.32 |
| 2004/0179976 | A1 * | 9/2004 | Chang | A61B 10/0038 422/534 |
| 2006/0122534 | A1 * | 6/2006 | Matsumura | A61B 10/0038 600/562 |
| 2007/0163366 | A1 * | 7/2007 | Jeong | G01N 1/14 73/864.87 |
| 2007/0287193 | A1 * | 12/2007 | Pressman | B01D 61/18 436/178 |
| 2010/0121046 | A1 * | 5/2010 | Ahlquist | A61B 10/0038 536/25.41 |
| 2011/0020860 | A1 * | 1/2011 | Greenwald | A61B 10/0038 435/34 |
| 2012/0037563 | A1 * | 2/2012 | Liao | A61B 10/0038 210/634 |
| 2012/0125125 | A1 * | 5/2012 | Li | A61B 10/0038 73/863 |
| 2014/0017720 | A1 * | 1/2014 | Sidorsky | A61J 1/00 435/30 |
| 2014/0238154 | A1 * | 8/2014 | Stevens | A61B 10/0038 73/863.52 |
| 2015/0072346 | A1 * | 3/2015 | Gellibolian | G01N 1/4077 435/6.11 |
| 2015/0090652 | A1 * | 4/2015 | Hensler | A61M 1/0056 210/232 |
| 2015/0118688 | A1 * | 4/2015 | Weidemaier | C12M 23/38 435/7.1 |
| 2015/0182736 | A1 * | 7/2015 | Salvador | A61F 5/44 604/514 |
| 2017/0030811 | A1 * | 2/2017 | Gellibolian | G01N 1/4077 |
| 2017/0273670 | A1 * | 9/2017 | Rostaing | A61B 10/0038 |

* cited by examiner

SYSTEMS, DEVICES, AND METHODS FOR SPECIMEN PREPARATION

CROSS REFERENCE TO RELATED APPLICATIONS

This application claims priority to U.S. Provisional Patent Application No. 62/162,144 filed May 15, 2015 in the name of Colleen Kraft, W. Robert Taylor, Michael L. Wach, Jonathan Shaw, and Louis F. Malice and entitled "Systems, Devices, and Methods for Specimen Preparation," the entire contents of which are hereby incorporated herein by reference. This application is related to U.S. Provisional Patent Application No. 62/099,653 filed Jan. 5, 2015 in the name of Colleen Kraft, W. Robert Taylor, and Michael L. Wach and entitled "System for Specimen Preparation," the entire contents of which are hereby incorporated herein by reference.

TECHNICAL FIELD

Embodiments of the technology relate to processing a fecal specimen to produce a preparation suitable for delivery into a digestive track of a patient in connection with treating a health condition.

BACKGROUND

Many processes for specimen preparation can hinder adoption of related use. For example, conventional preparation of fecal specimen for transplantation into the intestines of patients suffering from *Clostridium difficile* (C-diff) infection can be expensive, labor intensive, unhygienic, unslightly, among others. Additionally, there is no procedural standardization for preparation of a fecal specimen.

SUMMARY

Thus, there is a need for hygienic and economical methods, devices and systems for specimen preparation.

The disclosure relates to systems, devices, and methods for preparing a specimen. In some embodiments, a preparation device is configured to prepare a specimen. In some embodiments, the preparation device may include a preparation device configured to be attached to a specimen collection device. The preparation device may include an agitator member, a filter member, and a preparation platform member. The filter member and the agitator member may be configured to move independently with respect to each other and the preparation platform member. The filter member may be configured to move linearly with respect to the preparation platform member and the agitator member, and the agitator member may be configured to move linearly and radially with respect to the preparation platform member and the filter member.

In some embodiments, the preparation system may include the preparation device and a specimen collection device. The specimen may include but is not limited to fecal matter.

In some embodiments, the method may include disposing a sample within a specimen collection device. The method may also include attaching the preparation device to the specimen collection device. The preparation device may include an agitator member, a filter member, a preparation platform member and a filtrate member. The method may further include adding a solution to the specimen collection device and moving the filter member and/or agitator member to produce a filtrate. The method may also include removing the filtrate through the filtrate member. The specimen may include but is not limited to fecal matter.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DETAILED DESCRIPTION OF EXAMPLE EMBODIMENTS

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications.

The preparation devices, systems and methods according to embodiments may be configured to prepare any specimen, for example, for analysis (e.g., chemical, medical, etc.), a medical procedure, among others, or a combination thereof. Although the specimen is discussed with respect to a fecal sample, it will be understood that the specimen can be any biological sample, as well as other collected samples (e.g., soil, sewage material, etc.), or a combination thereof. It will also be understood that the device may prepare a specimen sample for uses other than fecal transplantation. It will also be understood that the dimensions, shape, etc. of the devices and systems may be adjusted for a specimen and/or a specific volume or range of volumes of a specimen.

Figure 1:
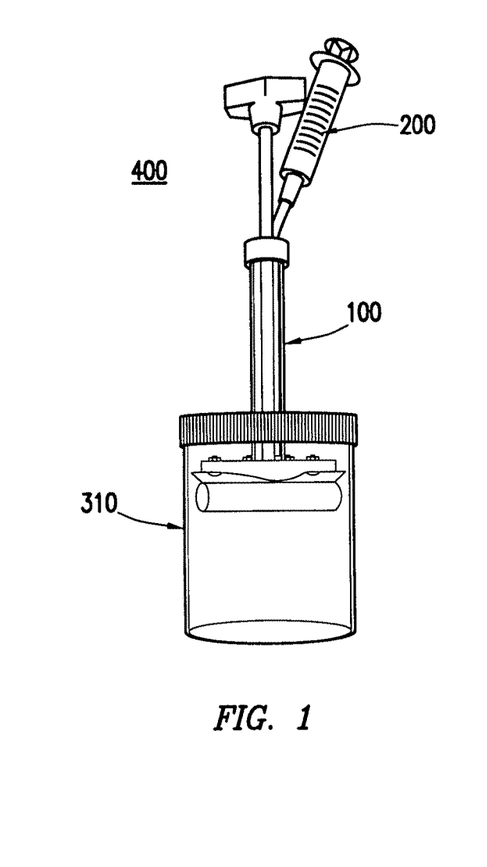
FIG. 1 shows a preparation system according to some embodiments.
Figure 2:
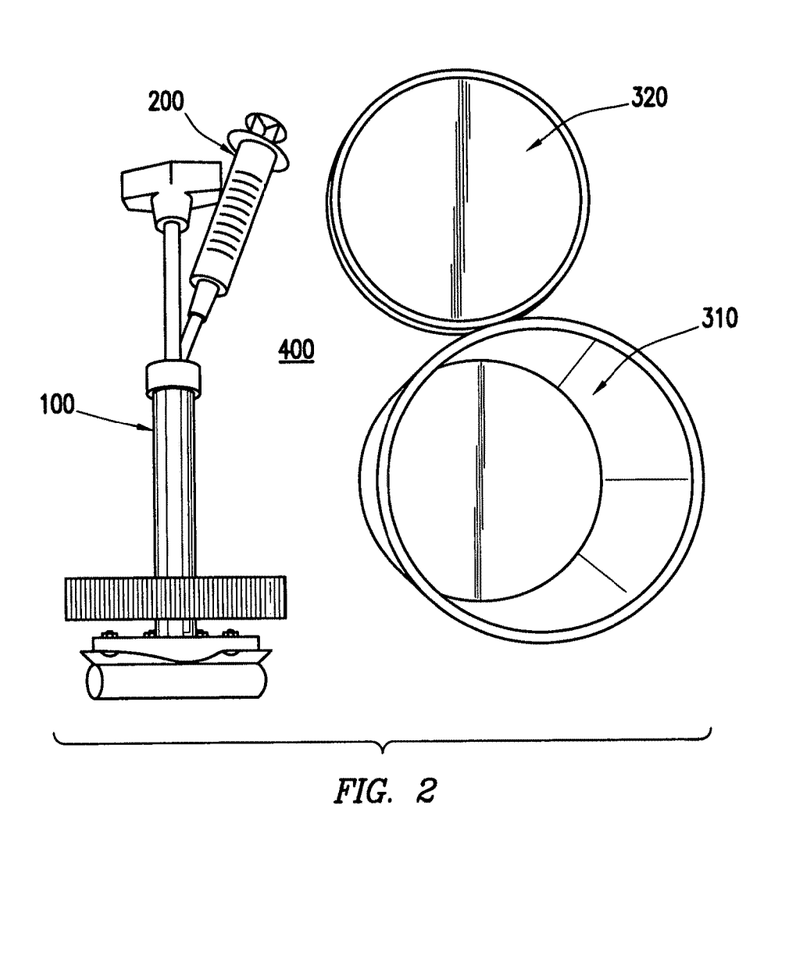
FIG. 2 shows another view of the preparation system shown in FIG. 1 according to some embodiments.
Figure 3:
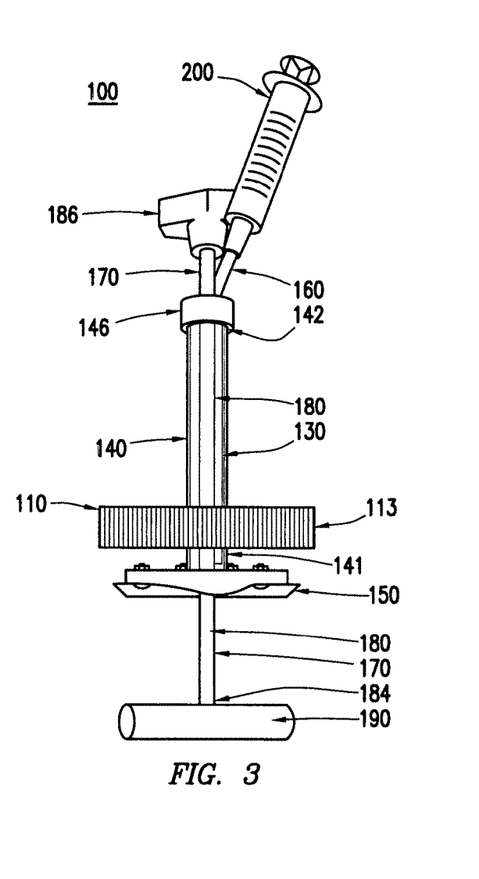
FIG. 3 a preparation device according to some embodiments.
Figure 4:
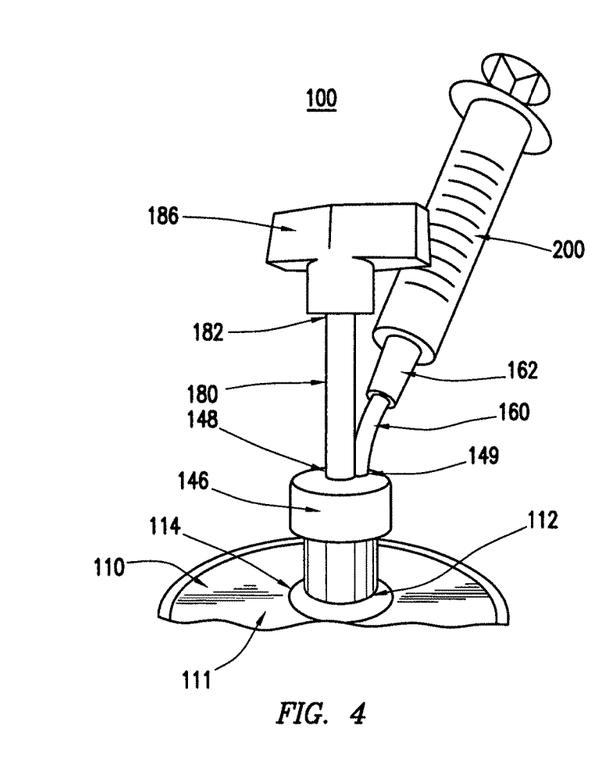
FIG. 4 shows another view of the preparation device shown in FIG. 3 according to some embodiments.
Figure 5:
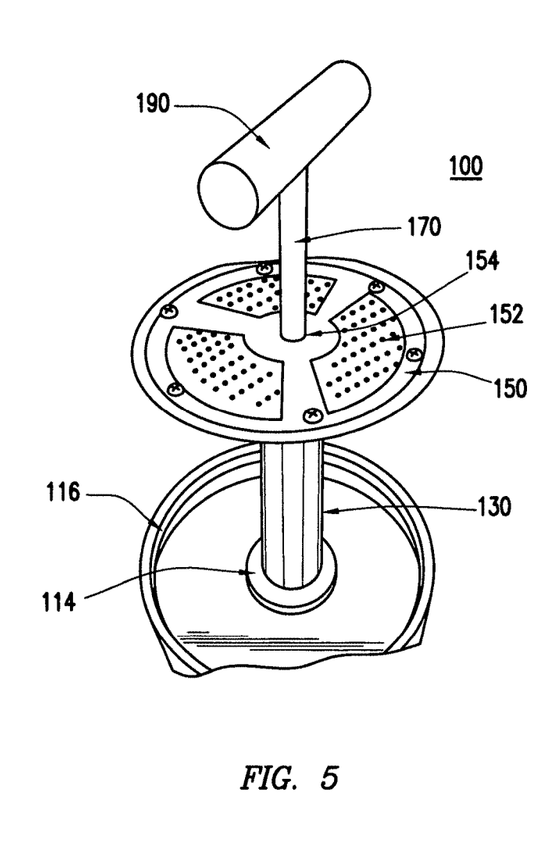
FIG. 5 shows another view of the preparation device shown in FIG. 3 according to some embodiments.
Figure 6:
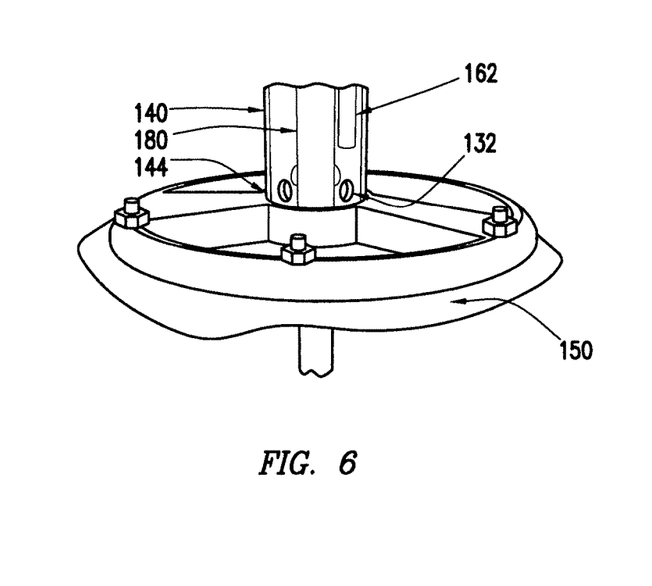
FIG. 6 shows another view of the preparation device shown in FIG. 3 according to some embodiments.
Figure 7:
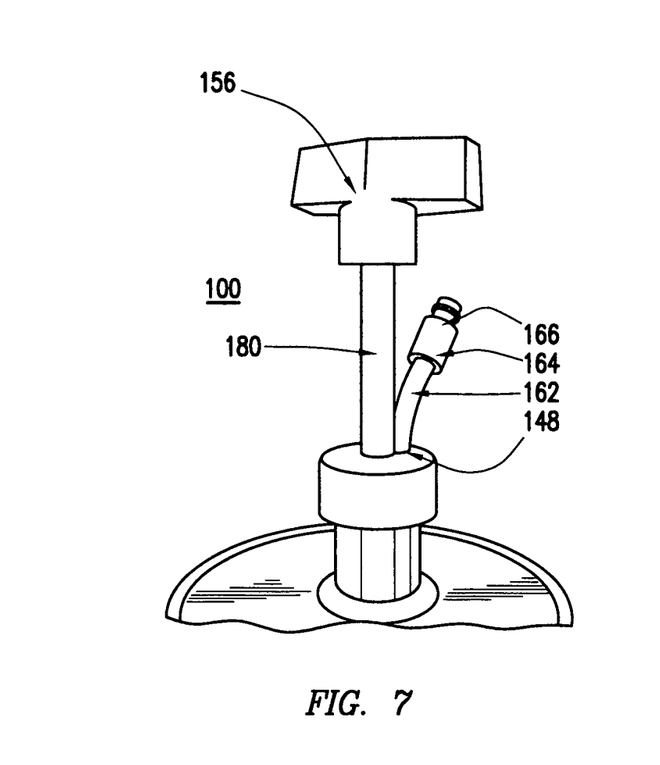
FIG. 7 shows another view of the preparation device shown in FIG. 3 according to some embodiments.

FIGS. 1 and 2 show a preparation system 400 configured to prepare a specimen. In some embodiments, the preparation system 400 may include a preparation device 100 configured to prepare a specimen and a specimen collection device 310. In some embodiment, the preparation system 100 may further include a syringe 200. It will be understood that the system 400 may omit and/or include further components. For example, the system 400 may omit the specimen collection device 300 and/or the syringe 200.

FIG. 1 shows the preparation device 100 mated with the specimen collection device 310. However, it will be understood that the preparation device 100 may be detached. The preparation device 100 may also be used with different specimen collection device 310 and is not limited to the specimen collection device 310 shown.

In some embodiments, the system 400 may further include a lid 320 for the specimen collection device 310 so that the specimen may be collected and transported in the specimen collection device.

FIGS. 3-7 show a preparation device 100 configured to prepare a specimen according to some embodiments. FIGS. 3-7 show the syringe 200 attached to the device 100. In some embodiments, the syringe 200 may be removably attached to the device 100. The syringe 200 may be any syringe. In further embodiments, the syringe 200 may be omitted.

The preparation device 100 may be configured to be attached to a specimen collection device (e.g., for example, the specimen collection device 310). For example, the preparation device 100 may be attached or mated to a specimen collection device that has been to collect the specimen. In this way, the specimen does not need to be moved from the specimen collection device for the specimen transportation and can remain in the specimen collection device from collection through specimen preparation, as well as during any transportation transport before and/or after the specimen preparation. The specimen may also remain sterile throughout the process. The preparation device 100 can therefore provide a hygienic means for processing at least partially biohazardious materials, such as fecal samples.

In some embodiments, the preparation device 100 may include a preparation platform 110 configured to attach the preparation device 100 to a specimen collection device (e.g., device 310) and a preparation member 130 configured to be movable with respect to the preparation platform member 110. The preparation platform member 110 may include a top surface 111 and a side surface 113. The preparation platform member 110 may include an opening 112 disposed in the top surface 111 and in which the preparation member 130 may be disposed. In some embodiments, the opening 112 may be disposed about the center of the top surface 111 of the preparation platform member 110. In other embodiments, the opening 112 may be disposed at a different location on the preparation platform 110.

In some embodiments, the device 100 may include a sealing member 114 configured to seal the opening 112 so that the preparation member 130 can move with respect to the preparation platform 110 without allowing fluid to pass to the outside of the device. In some embodiments, the sealing member 114 may be disposed within the opening 112 so that it surrounds the preparation member 130. In some embodiments, the sealing member 114 may be a rubber seal. In other embodiments, other sealing members may be used.

In some embodiments, the preparation platform member 110 may be include one or more fastening members 116 configured to sealingly mate the preparation device 100 to a specimen collection device (e.g., the device 310). In some embodiments, the one or more fastening members 116 may be groves/threads disposed along the inner circumference of the side surface 113 so that preparation platform 110 may be screwed onto a specimen collection device. The one or more fastening members 116 may be complimentary to the fastening members of the specimen collection device to which the preparation device 100 is designed to be attached. For example, the preparation device 100 may be configured to be snapped onto a specimen collection device.

In some embodiments, the preparation platform member 110 may have a circular shape. In other embodiments, the preparation platform 110 may have a different shape, for example, that corresponds to a specimen collection device.

In some embodiments, the length of the side surface 114 may be correspond to the complimentary portion of the specimen collection device to be attached. In other embodiments, the side surface 114 may be longer so as to provide more sealing surface area.

In some embodiments, the preparation platform member 110 may include one or more vents (not shown) disposed on the top surface 113. The one or more vents can be configured to allow air past but not fluid so that fluid may be drawn from an attached specimen collection device during and/or after the preparation of the specimen.

In some embodiments, the preparation device 100 may include a filter member 130 and an agitator member 170. The filter member 130 and the agitator member 170 may be configured to move with respect to each other and/or the preparation platform 110. In some embodiments, the preparation device 100 may include a filtrate member 160 fixed with respect to the filter member 130 and/or the preparation platform 110.

In some embodiments, the filter member 130 may include an extending member 140 having a first end 142 and a second end 144. In some embodiments, the extending member 140 may be a hollow channel, for example, a tube. In some embodiments, the extending member 140 may be transparent. In other embodiments, the extending member 140 may be opaque or another color.

In some embodiments, the filter member 130 may include a cap 146 disposed at the first end 142 of the extending member 140. The cap 146 may include one or more openings for the agitator member 170, the filtrate member 160, and/or other components. In some embodiments, the cap 146 may include an opening 148 through which the agitator member 170 may be disposed and an opening 149 through which the filtrate member 160 may be disposed. In some embodiments, each of the openings may be offset from a center of the cap 146. In some embodiments, the cap 146 may include additional openings. In some embodiments, the cap 146 and openings 146, 148 may be configured to be water tight so as to not allow fluid to pass the agitator member 170 and/or the filtrate member 160.

In some embodiments, the filter member 130 may include a filter 150 disposed at the second end 144. The extending member 140 may be configured to linearly move the filter 150 with respect to the preparation platform 110, an attached specimen collection device (e.g., toward and away from the attached specimen collection device), and/or the agitator member 170. In some embodiments, the extending member 140 may additionally or alternatively be configured to radially move with respect to the preparation platform 110, the agitator member 170 and/or an attached specimen collection device (e.g., the device 310).

In some embodiments, the filter 150 may be configured to press against a specimen disposed in an attached specimen collection device. In this way, the filter 150 can be configured to trap particulates at the bottom of a specimen collection device.

In some embodiments, the filter 150 may have any shape. In some embodiments, the shape of the filter 150 may correspond to the shape of the specimen collection device to be attached to the preparation device 100. For example, the filter 150 may have a circular shape. In some embodiments, the diameter of the filter 150 may be sized such that the filter 150 runs flush against the wall of the specimen collection device.

In some embodiments, the filter member 130 may be configured such that the filter member 130 may include a mechanism to restricted movement in one or more directions. In some embodiments, the filter member 130 may be configured to have resistance when pulled up (away from a specimen collection device and the preparation platform). In some embodiments, the size of the filter 150 may be such that upward movement may be restricted. In other embodiments, the preparation device 100 may include other mechanisms.

In some embodiments, the filter 150 may include a plurality of filtering holes 152. In some embodiments, the filtering holes 152 may be configured to allow fluid to pass but not solid material. For example, for a fecal specimen, the filtering holes 152 may be configured to allow fluid but not solid fecal matter to pass. In other embodiments, other filters may be used. In some embodiments, the size, shape, spacing, and/or number of the filtering holes 152 may depend on the specimen to be prepared.

In some embodiments, the filter 150 may include an opening 154. In some embodiments, the opening 154 may be disposed substantially in the center of the filter 150. In other embodiments, the opening 154 may be offset from the center of the filter 150. The opening 154 may be configured to the diameter of the agitator member 170 (i.e., the extending rod 180) so that the agitator member 170 can move linearly and radially with respect to the filter member 130.

In some embodiments, the filter member 130 may include a plurality of openings 132 disposed along the circumference of the extending member 140 near the second end 144. The openings 132 may be spaced apart. The plurality of openings 132 may be disposed above the filter 150 with respect to the first end 142. The plurality of openings 132 may have any size, number, spacing, and/or shape. In some embodiments, the openings may depend on the particulate to be drawn. In some embodiments, the openings 132 may have a circular shape. In some embodiments, the openings 132 may be configured to allow fluid disposed above the filter 150 in a specimen collection device to be drawn into the extending member 140 and/or the filtrate member 160.

Figure 9:
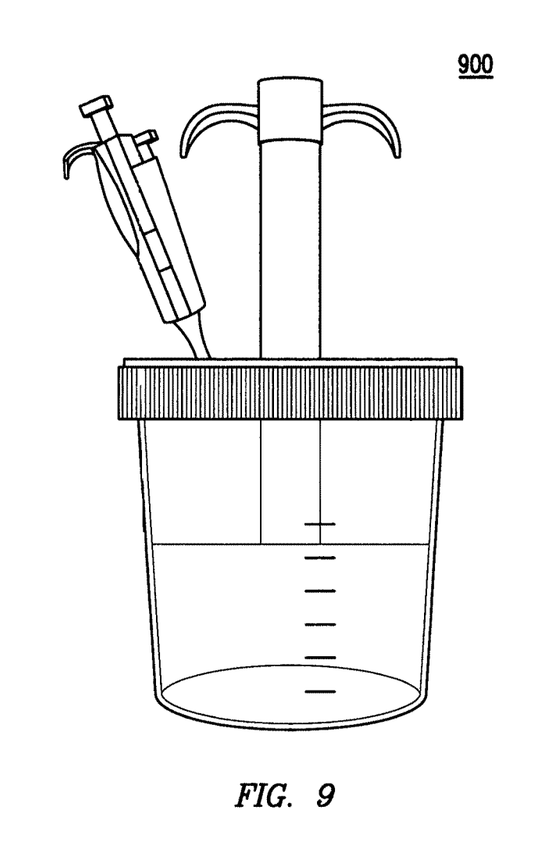
FIG. 9 shows an example of a preparation system according to embodiments.

In some embodiments, the agitator member 170 may include an extending rod member 180 having a first end 182 and a second end 184 and an agitator 190 disposed at the second end 184. In some embodiments, the agitator member 170 may include a handle 186 disposed at the first end 182. In some embodiments, the handle 186 may have any shape. In some embodiments, the handle 186 may ergonomic. In some embodiments, the handle 186 may have one or more grip sections. In some embodiments, the handle 186 may have a T-shape. For example, the handle 186 may have two sections grip sections on opposing sides of the extending rod 140 that are substantially linear. In other embodiments, the handle 186 may have two grip sections that are concave and/or convex. For example, FIG. 9 shows a preparation system 900 with handle having convex grip sections.

In some embodiments, the rod member 180 may be configured to linearly and radially move the agitator 190 with respect to the preparation platform member 110, the extending member 140 and/or an attached specimen collection device. In some embodiments, the agitator 190 may be configured to cut through, breakup and/or agitate a specimen disposed in an attached specimen collection device (e.g., the device 310).

In some embodiments, the rod member 180 may be disposed within the extending member 140 of the filter member 130 and through the opening 152 of the filter 150 and the opening 148 of the cap 146. In some embodiments, the rod member 180 may be a press rod. In other embodiments, the rod member 180 may be different. The agitator 190 may be disposed below the filter 150 and the handle 186 may be disposed above the cap 146. In this way, in use, the filter 150 may limited the linear movement of the agitator 190 with respect to an attached specimen collection device.

In some embodiments, the agitator 190 may be made of any material (e.g., flexible, semi-flexible, or rigid material). In some embodiments, the agitator 190 may have any shape. For example, the agitator 190 may have an elongated shape, as shown in FIGS. 3-7.

Figure 8A:
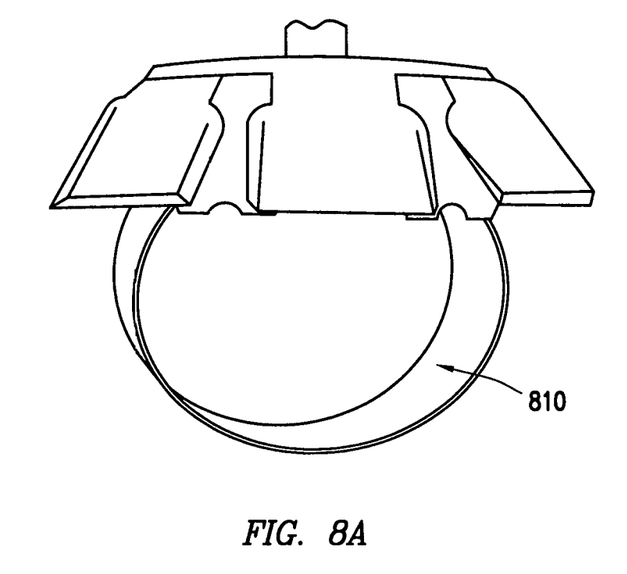
FIGS. 8A and 8B show agitators according to embodiments.
Figure 8B:
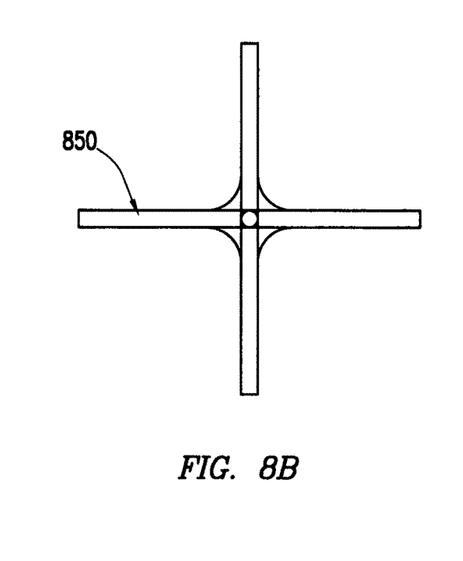

In some embodiments, the agitator may have a different configuration and/or shape. FIGS. 8 and 8B show examples of other agitators according to embodiments. FIG. 8A shows an example of an agitator 810 that is a flexible band. The agitator 810 may be made of a flexible plastic. The agitator 810 may be configured to translate rotational force and collapse when the extendible member is pressed fully down. In this way, the band can translate torque effectively but not linear force.

In some embodiments, the agitator may include one or more radially extending and angled blade-like members. FIG. 8B shows an example of an agitator 850 having radially extending members. In some embodiments, the diameter of the agitator 850 may be of a size such that the agitator 850 can move radially without hitting sides of the attached specimen collection device.

In another example, the agitator may be a collapsible wire, a whisk-like shape, a low-profile blade, one or more tines, prongs, or the like, among others, or a combination thereof.

In some embodiments, the filtrate member 160 may be configured to facilitate the drawing out and/or removal of the prepared specimen (e.g., filtrate) from an attached specimen collection device (e.g., the device 310) and/or delivery of a solution (e.g., a saline solution) to a specimen disposed in the attached specimen collection device. The filtrate member 160 may include tubing 162 having a first end 164 and a second end 166 and a length therebetween. A portion of the length of the tubing 162 may be disposed within the extending member 130 adjacent to the rod member 180 and the parallel to the extending member 140. In some embodiments, the second end 166 may be disposed within the extending member 140 near and/or above the openings 132. The tubing 162 may be open at both ends. In some embodiments, the filtrate member 160 may include a tube fitting 166 (e.g., Luer-Lok) disposed at the first end 162. The tube fitting 166 may be configured to attach to a filtrate removal device, such as the syringe 200 and/or a peristaltic pump (e.g., via tubing)(not shown). The filtrate member 160 can be configured to be used to draw out the prepared specimen (e.g., filtrate), for example, with the syringe 200 or peristaltic pump from an attached specimen collection device through the openings 132. In some embodiments, the fitting 166 may be configured to attach to a channel of an instrument, for example, a GI endoscope to facilitate a fecal transplant procedure, either directly or via an intervening section of flexible tubing.

In some embodiments, the filtrate member 160 may include a filter disposed at the second end 164 (not shown). In some embodiments, one or more filters may be disposed on the extending member 130 to cover the plurality of openings 132 (not shown). In such embodiments, the fluid that is drawn up can be filtered twice—first by the filter 150 when the filter 150 is pressed downward in the attached specimen collection device and second when the fluid is sucked through the filtrate member 160.

In some embodiments, the rod 180 of the agitator member 170 may be disposed with respect to the filter member 130 so as to extend through the extending member 140, the opening 148 of the cap 146 and the opening 112 of the filter 150. Because the opening 148 is offset, the agitator member 180 may be offset from the center of the preparation platform 110 and/or center of an attached specimen collection device. The openings 148 and 112 may act as a mechanism that maintains the position of the agitator member 180 with respect to the extending member 140, the filter 150, the preparation platform 110, and/or an attached specimen collection device when the agitator member 170 is moving linearly and/or radially, and/or the filter member 130 is moving linearly. In some embodiments, the tubing 162 of the filtrate member 160 may extend through 149 of the cap to a location within the extending member 140. Because the opening 149 is offset, the agitator member 180 may be offset from the center of the preparation platform 110 and/or the center of an attached specimen collection device. The opening 149 may act as a mechanism that maintains the position of the agitator member 170 with respect to the extending member 140, the filter 150, the preparation platform 110 and/or an attached specimen collection device when the agitator member 180 is moving linearly and/or radially, and/or the filter member 130 is moving linearly.

In use, the filter member 130 and the agitator member 170 may be configured to independently move with respect to each other and/or an attached specimen collection device. The agitator member 170 may be configured to be moved radially and linearly with respect to the preparation platform 110 and/or an attached specimen collection device (e.g., device 310) while the filter member 130 can be configured to move only linearly (e.g., rotationally/radially stationary with respect to the preparation platform 110 and/or the agitator member 170 and/or the attached specimen collection device). This can help keep the filter from clogging.

In some embodiments, the length of the extending member 140 may be shorter than the length of the rod 180 so that the agitator member 170 may be move past the filter member 130 when the preparation device is attached to a specimen collection device and the filter member 130 is engaged (e.g., pushed down). In some embodiments, the length of the rod 180 and/or the extending member 140 may depend on the size of the specimen collection device to be attached or mated to the preparation device 100.

In some embodiments, the agitator member 170 and the filter member 130 may have a different structure and/or configuration that allow the filter member and the agitator member to move independently with respect to each other.

In some embodiments, the rod member 180 of the agitator member 170 may include a helical twist along the length. For example, the corners of the square cross section of the extending member may form a helix along the length of the extending member. In this example, the square cross section taken at one point along the length of the extending member can be rotated relative to the square cross section taken at another point along the length of the rod member. In such an embodiment, when a user manually presses the extending member through the aperture, the helical twist may produce rotation of the rod member, thereby rotating the agitator. Thus, when the user reciprocates the rod member, the agitator can spin clockwise on the down-stroke and counterclockwise on the upstroke (or vice versa) to agitate and mix the specimen, for example, fecal matter and saline.

In use, the system may be used for preparing a specimen, for example, a fecal sample for a fecal transplant. In one example, the fecal sample (e.g., stool) can be collected, transported, and stored in a specimen collection device, consistent with common stool collection for diagnostics. To process the stool for transplantation, the lid can be removed from the specimen collection device and the preparation device 100 may be attached to the specimen collection device. The preparation device can filter out stool particulates so that the filtrate can be infused into the patient through a channel of an endoscope. For example, a clinician can draw the filtrate into the syringe through the filtrate member 160 by drawing the filtrate on the opposite side of the filter 150 through the openings 132 of the extending member 130. The syringe can be disconnected from the filtrate member 160 and connected to a corresponding port in an endoscope. The clinician then can readily administer the filtrate through a channel of the endoscope by depressing the syringe plunger. Alternatively, in some embodiments, the filtrate member 160 can be connected to an endoscope port via flexible tubing, and pumped through a channel of the endoscope and into a patient's colon using a peristaltic pump.

In some embodiments, one or more components of the system may be sterilized. In some embodiments, one or more parts of the system may be reused. In further embodiments, one or more parts of the system may be disposable. In further embodiments, the system may be a single, use device.

In some embodiments, the system may be part of one or more kits. In some embodiments, the one or more kits may include the preparation device. In some embodiments, the one or more kits may further include a specimen collection device to be mated and/or attached with the preparation device and one or more lids for the specimen collection device. In some embodiments, for example, for fecal specimen preparation, the one or more kits may also include a one or for syringes configured for the filtrate member for drawing the particulate from the specimen collection device; a fluid for the specimen preparation (e.g., saline solution); a peristaltic pump tube for hookup with endoscopic spray nozzle; a toilet hat for specimen collection, a measuring scoop for specimen collection; gloves; among others; or a combination thereof. In some embodiments, the one or more kits may include a kit with components for a clinician responsible for preparing the specimen (e.g., a healthcare staff member); a kit with components for the user responsible for collecting the specimen (e.g., specimen donor).

In some embodiments, the system may omit an agitator member. In these embodiments, the system may include one or more agitator objects (e.g., one or more irregularly shaped objects) that can be added to specimen-liquid (e.g., fecal-saline) composition.

While the disclosure has been described in detail with reference to exemplary embodiments, those skilled in the art will appreciate that various modifications and substitutions can be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A system for processing fecal matter to produce a preparation suitable for delivery into a patient, the system comprising:
   a container that is sized for collecting a fecal matter specimen and that comprises:
      a bottom;
      a threaded mouth; and
      a sidewall that extends between the bottom and the threaded mouth and that extends around an axis;
   a first lid that is threaded to mate with the threaded mouth of the container for storing the fecal matter specimen in the container; and
   a preparation device that comprises:
      a second lid comprising:
         a first aperture disposed on the axis;
         a seal disposed at the first aperture;
         a lower side that comprises threads configured to mate with the threaded mouth of the container when the first lid is removed from the container; and
         an upper side disposed opposite the lower side;
      a tube that extends along the axis and through the first aperture so that a first portion of the tube is disposed on the upper side of the second lid and a second portion of the tube is disposed on the lower side of the second lid, wherein the tube is configured to move linearly through the first aperture along the axis so as to decrease the first portion of the tube while increasing the second portion of the tube;
      a filter that is attached to a lower end of the second portion of the tube, that is sized according to the sidewall, and that comprises a second aperture;
      an opening in a side of the tube, the opening disposed adjacent the filter and above the filter;
      a cap that is disposed at an upper end of the first portion of the tube and that comprises a third aperture;
      a rod that extends along the axis through the tube, through the first aperture of the second lid, through the second aperture of the filter, and through the third aperture of the cap, wherein the rod is configured to move linearly and rotationally relative to the filter, the tube, and the second lid, the rod comprising a top end and a bottom end;
      an agitator attached to the bottom end of the rod;
      a handle attached to the top end of the rod and sized to facilitate manual rotation and linear motion of the rod;
      a lumen that extends between the opening in the tube and the cap; and
      a syringe that mates with the tubing for drawing filtrate up the tubing.

2. The system according to claim 1, wherein the lumen comprises a second tube that is disposed in the tube.

3. The system according to claim 1, wherein the lumen is disposed inside the tube.

4. The system according to claim 1, wherein the sidewall of the container is cylindrical and tapered, and the filter is circular and comprises a rim that extends along the sidewall.

5. The system according to claim 1, wherein the second lid comprises a vent.

6. The system according to claim 1, wherein the rod comprises a helical twist for converting linear force applied to the rod into rotational motion of the agitator.

* * * * *